United States Patent

Takeuchi

Patent Number: 5,840,033
Date of Patent: Nov. 24, 1998

[54] METHOD AND APPARATUS FOR ULTRASOUND IMAGING

[75] Inventor: Yasuhito Takeuchi, Tokyo, Japan

[73] Assignee: GE Yokogawa Medical Systems, Limited, Tokyo, Japan

[21] Appl. No.: 857,450

[22] Filed: May 16, 1997

[51] Int. Cl.$^6$ .................................................. A61B 8/00
[52] U.S. Cl. ........................ 600/443; 128/916; 600/455
[58] Field of Search ............................ 128/916; 600/443, 600/455, 441

[56] References Cited

U.S. PATENT DOCUMENTS

| | | |
|---|---|---|
| 4,543,829 | 10/1985 | Lerch . |
| 4,570,488 | 2/1986 | Miwa et al. ............................ 128/916 |
| 5,090,412 | 2/1992 | Shimazaki . |
| 5,322,067 | 6/1994 | Pratet et al. ........................... 128/916 |
| 5,375,600 | 12/1994 | Melton, Jr. et al. .................... 600/455 |
| 5,379,769 | 1/1995 | Ito et al. ................................. 128/916 |
| 5,460,181 | 10/1995 | Syed-Bolorforosh ................... 128/916 |
| 5,601,084 | 2/1997 | Sheehan et al. ........................ 600/443 |
| 5,669,385 | 9/1997 | Pesque et al. .......................... 128/916 |

FOREIGN PATENT DOCUMENTS

| | | |
|---|---|---|
| 335578 | 10/1989 | European Pat. Off. . |
| 394439 | 10/1990 | European Pat. Off. . |

*Primary Examiner*—Marvin M. Lateef
*Assistant Examiner*—Maulin Patel
*Attorney, Agent, or Firm*—Moonray Kojima

[57] ABSTRACT

A method and apparatus for ultrasonically producing 3-dimensional images in real time, wherein a device transmits an ultrasonic wave toward a solid bearing angle obtained by dividing into multiple portions a solid bearing angle subtended by a sonic field to be examined, and receives echoes therefrom, with the transmitted waves being sequential and the received echoes being concurrent multiple waves from each small solid angle, and a device for producing the 3-dimensional images by range gating the received echo signals in the depth direction of the sonic field being examined and then producing direct vision images in the direction of the transmitted ultrasonic waves based on the echo signals, wherein the range gated signals are quadrature detected in one embodiment and/or are subjected to 2-dimensional Fourier transformation in another embodiment.

8 Claims, 6 Drawing Sheets

METHOD AND APPARATUS FOR ULTRASOUND IMAGING

FIELD OF THE INVENTION

The present invention relates to an ultrasound imaging method and apparatus for producing 3-dimensional images in real-time.

BACKGROUND OF THE INVENTION

An ultrasound imaging system transmits ultrasound to a subject, receives the reflected waves (echoes), and produces images of the interior of the subject based on the echo data. Ultrasound is transmitted and received in directional beam (sound ray). A desired region to be imaged inside a subject is scanned by the sound ray-sequential transmittion and reception of ultrasound, and the received signals necessary to produce images are acquired.

When the 3-dimensional images are to be produced, a 3-dimensional region in the sound field is scanned, and the acquired echo data therefrom is used to produce the images.

In order to display the real-time 3-dimensional images, the image display speed (frame rate) on the order of 20—30 FPS (frame per second) is required. Thus, the echo data sufficient to produce one frame per 30–50 ms must be acquired.

However, since the sound velocity inside a subject is limited, when the sound ray-sequential scanning is employed no more than about 100 sound rays can be transmitted/received in such a period of time. If the scanning is performed using such a few sound rays, to attain practical spatial resolution would result in the limited 3-dimensional region to be scanned, while to extend the 3-dimensional region up to the practical size would result in the reduction in the sound ray density and the spatial resolution of the image, neither of which are suitable for practical use.

SUMMARY OF THE INVENTION

It is therefore an object of the present invention to provide an ultrasonic imaging method and apparatus for producing 3-dimensional images in real-time.

In the first aspect, the present invention provides a method for ultrasound imaging, comprising: transmitting ultrasound to the interior of a subject for each of small solid bearing angles, said small solid bearing angles being obtained by dividing a solid bearing angle corresponding to an object to be imaged into multiple portions; receiving simultaneously echoes from said subject in a plurality of sound rays from each of said small solid bearing angles; range gating the received signals of said sound rays in the depth direction of said subject; and producing images of said subject at a predetermined depth and thickness based on said range gated signals.

In order to obtain images with high spatial resolution, the above-described method preferably further comprises: quadrature detecting said range gated received signals respectively; and 2-dimensional Fourier transforming said quadrature detected received signals of the plurality of sound rays in the bearing angle direction.

In the second aspect, the present invention provides an apparatus for ultrasound imaging, comprising: means for transmitting/receiving ultrasound, said means transmitting ultrasound to the interior of a subject for each of small solid bearing angles, said small solid bearing angles being obtained by dividing a solid bearing angle corresponding to an object to be imaged into multiple portions, and receiving simultaneously echoes from said subject as a plurality of sound rays from each of said small solid bearing angles; means for range gating the received signals of said sound rays in the depth direction of said subject; and means for producing images of said subject at a predetermined depth and thickness based on said range gated signals.

In the third aspect, the present invention provides an apparatus for ultrasound imaging, wherein said means for producing images in the above-constructed ultrasonic imaging apparatus further comprises: means for quadrature detecting said range gated received signals respectively; and means for 2-dimensional Fourier transforming said quadrature detected received signals of the plurality of sound rays in the bearing angle direction.

In accordance with the present invention, the 3-dimensional images of an object can be produced in real-time by scanning the sound field to be examined sequentially for each small solid bearing angle; receiving echoes in multi-beam; and producing direct vision images in the sound ray direction based on the echoes.

Further objects and advantages of the present invention will be apparent from the following description of the preferred embodiments of the invention as illustrated in accompanying drawings.

DETAILED DESCRIPTION OF THE INVENTION

Figure 1:
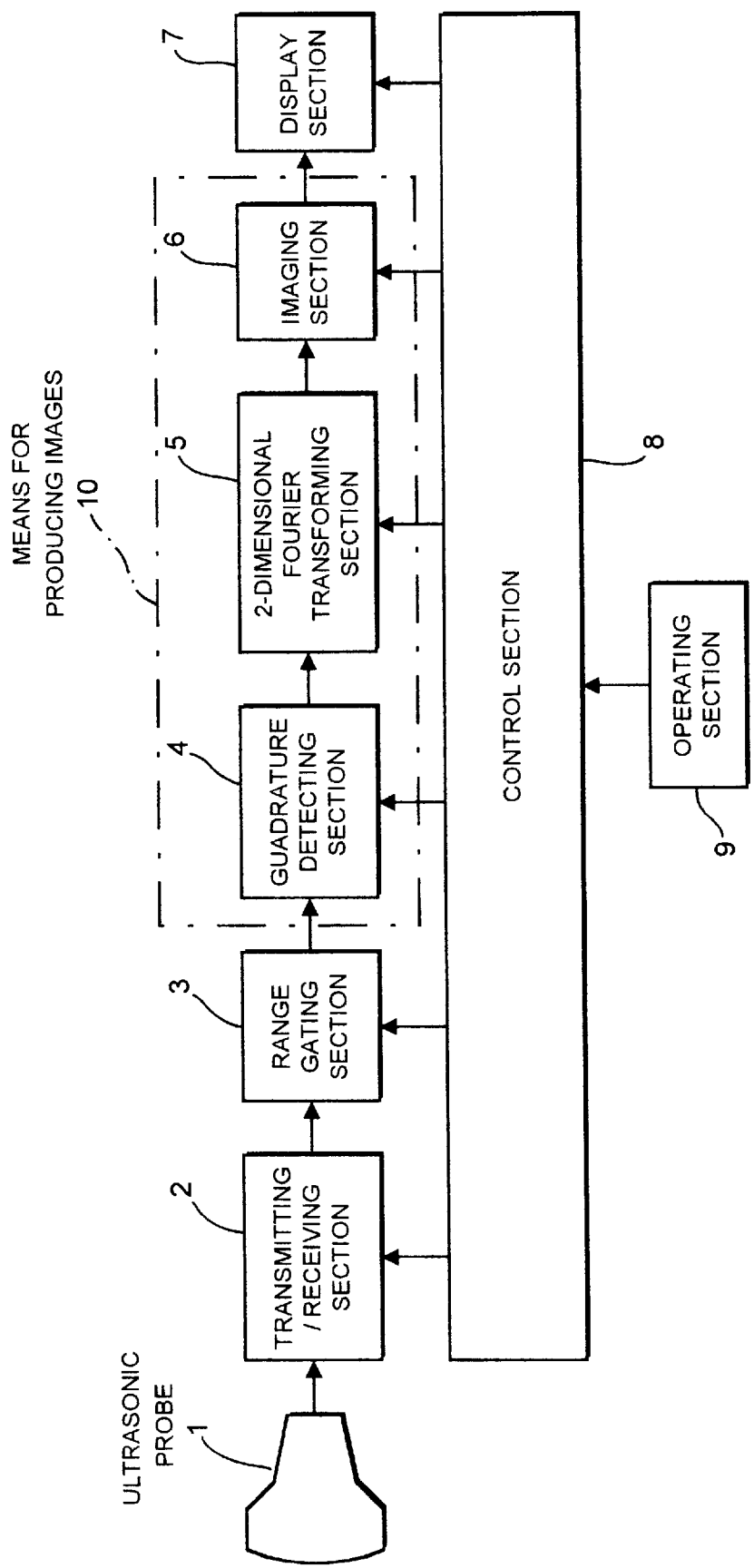
FIG. 1 is a block diagram of an apparatus of one embodiment of the present invention.

Referring to FIG. 1, there is shown a block diagram of an ultrasonic imaging apparatus, which is one embodiment of the present invention. The arrangement of the apparatus represents one embodiment of an apparatus in accordance with the present invention, and the operation thereof represents one embodiment of a method in accordance with the present invention.

In FIG. 1, an ultrasonic probe 1 transmits an ultrasonic beam to the sound field to be examined (not shown) and receives echoes therefrom. The ultrasonic probe 1 comprises, for example, a 2-dimensional array of a plurality of transducer elements.

Figure 2:
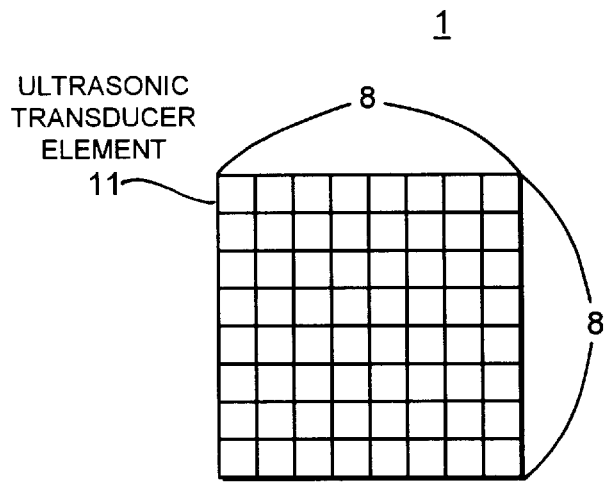
FIG. 2 is a view illustrating the arrangement of a transducer array in an ultrasonic probe in an apparatus of one embodiment of the present invention.

Referring to FIG. 2, there is shown an example of the transducer array in the ultrasonic probe 1. As shown in the drawing, the 2-dimensional array is comprised of, for example, 64 ultrasonic transducer elements 11 in an 8×8 matrix. The ultrasonic transducer elements 11 are constructed of piezoelectric materials such as PZT (lead zirconate titanate) and supported by backing materials (not shown).

A transmitting/receiving section 2 activates the ultrasonic probe 1 to transmit ultrasonic beams and receives echo signals detected by the ultrasonic probe 1.

Figure 3A:
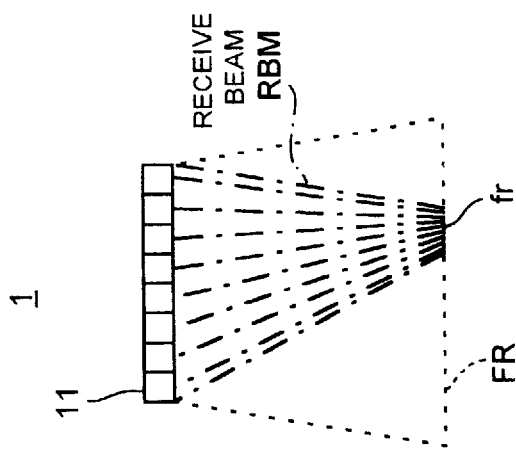
FIG. 3 is a view illustrating the ultrasound transmission/reception in an apparatus of one embodiment of the present invention.
Figure 3B:
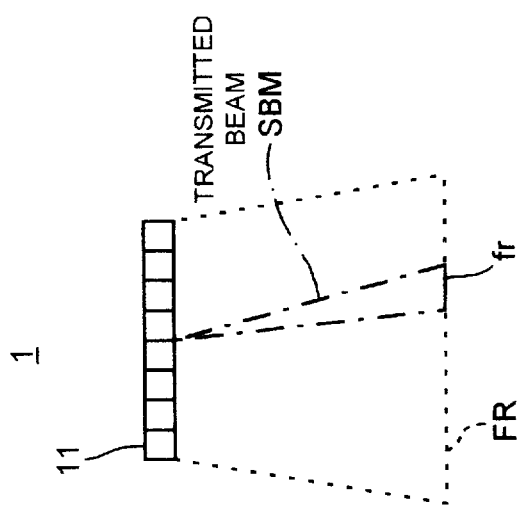
Figure 3C:
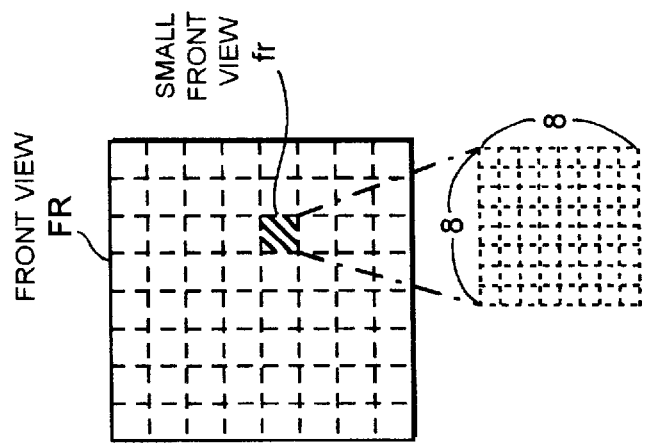

FIG. 3 is a schematic view of the ultrasound transmission/reception, wherein (a) is a plan view, and (b) and (c) are side views.

As shown in (a), for example, a front view FR from the ultrasonic probe 1 is determined in the sound field to be examined. The front view FR is a 2-dimensional view of the 3-dimensional region to be imaged from the front. The term "front" refers to a plane in the sound field to be examined, viewed straightforward in the sound ray direction. The solid angle which the front view FR subtends at the ultrasonic probe 1 provides a solid bearing angle of the front view.

A small front view fr is determined in the front view FR. The small front view fr is geometrically similar to the front view FR and, for example, reduced to a scale of ⅛ of the front view FR. The solid angle which the small front view fr subtends at the ultrasonic probe 1 provides a small solid bearing angle of the small front view.

In transmission, as shown in (b), an ultrasonic beam SBM having the thickness to contain the entire small front view fr is transmitted or sent to the small front view fr. Such a transmitted or sent beam SBM is formed by the transmission beam forming at the transmitting/receiving section 2 in the form of a cone beam or a fan beam, for example.

The corresponding echoes are received in a plurality of receive beams RBM as shown in (c). The plurality of receive beams RBM are formed by the reception beam forming at the transmitting/receiving section 2. Thus, the received echo signals along the sound rays (e.g., 64 rays) which are distributed uniformly in the small front view fr can be acquired in parallel.

When the small front view fr is represented as an 8 ×8 matrix as shown in (a), the above-described received echo signals correspond to the echo signals from the respective matrix elements. This means that the received signals which represent the small front view fr in an 8×8 matrix can be acquired at once in one transmission/reception.

The ultrasonic beam transmission/reception is repeated shifting sequentially the small front view fr to the adjacent region. This sequential shifting of the small front view fr is accomplished by the sequential switching of the transmission/reception beam forming at the transmitting/receiving section 2.

The front view FR is thus scanned sequentially for each small front view fr in 2 dimensions, and when the scale of the small front view fr is ⅛ of the front view FR, the entire front view FR is scanned by 64 transmission/receptions.

By scanning as above, the 3-dimensional sound field to be examined which has, for example, the 10cm×10cm front view FR and 10cm in depth can be scanned at the frame rate of, for example, 30FPS. In this case, the received echo signals of 64×64=4096 sound rays per frame are acquired.

That is, the received echo signals which correspond to, for example, the 10cm×10cm front view scanned with 64×64= 4096 sound rays can be acquired at the frame rate of 30 FPS.

The echo signals received by the transmitting/receiving section 2 are supplied into a range gating section 3. The range gating section 3 performs the range gating of the supplied received echo signals for the respective sound rays.

Figure 4:
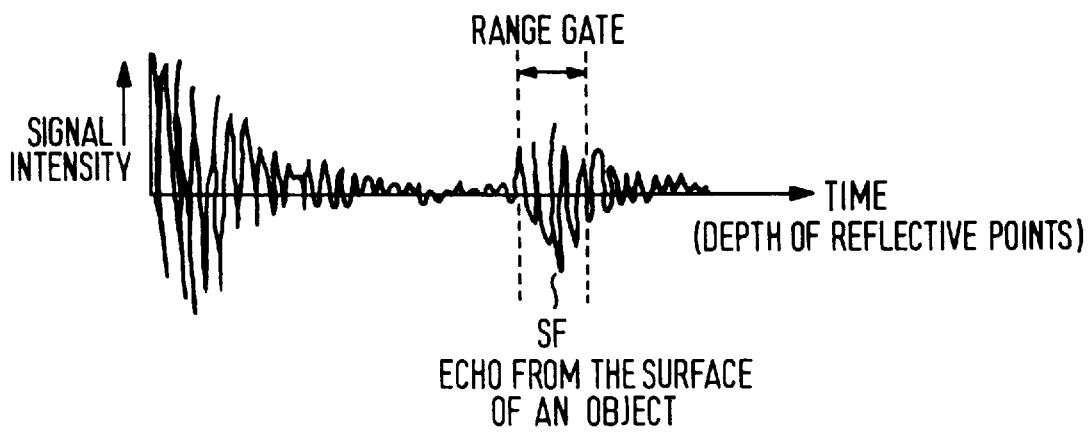
FIG. 4 is a wave form chart of received echo signals in an apparatus of one embodiment of the present invention.

The range gating cuts out from the received echo signal a signal fraction SF over the desired depth as shown in FIG. 4.

Figure 5:
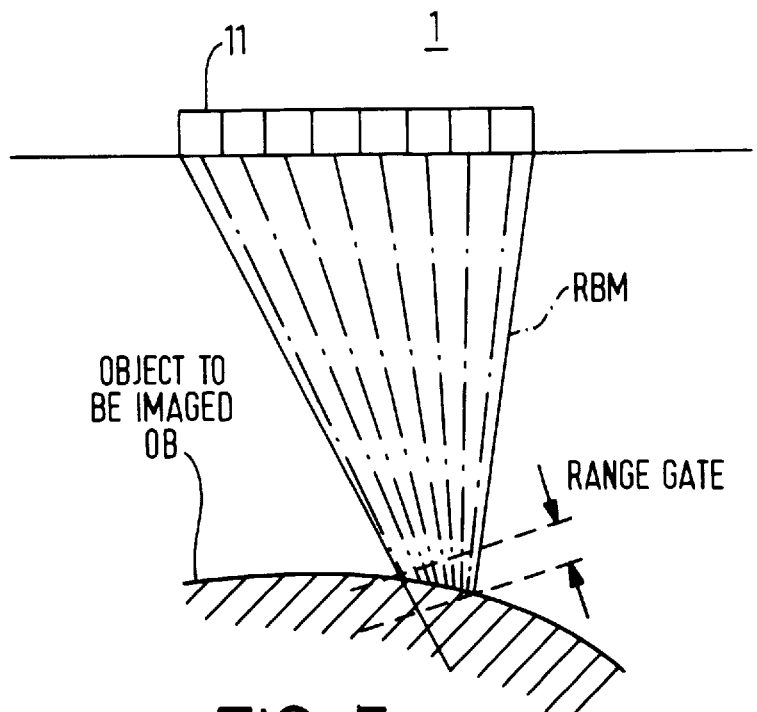
FIG. 5 is a view illustrating the operating mode of an apparatus of one embodiment of the present invention.

The signal fraction SF is, for example, the echo reflected from the surface of an object to be imaged OB in the sound field to be examined as shown in FIG. 5, and the timing and range of the range gate are controlled so that the desired signal fraction is cut out. As an example, the signal fraction SF is the echo from the body surface on a fetus in amniotic fluid inside a uterus.

Since the acoustic impedance of a fetus and that of amniotic fluid are considerably different, the range gating is performed based on the skin-trigger technique in the same manner as the conventional ultrasonic imaging technique using a water bag. The range gating by the skin-trigger technique is desirable with regard to its convenience.

The range gated received echo signals are quadrature detected and separated into a in-phase component i and a quadrature component q at a quadrature detecting section 4. The quadrature detecting section 4 is one embodiment of means for quadrature detecting in accordance with the present invention. The received echo signals of the respective sound rays which have been separated into the in-phase component i and quadrature component q are supplied into a 2-dimensional Fourier transforming section 5.

The 2-dimensional Fourier transforming section 5 performs the 2-dimensional Fourier transformation of the supplied received echo signals for all of the sound rays in the bearing angle direction. The 2-dimensional Fourier transforming section 5 is one embodiment of means for 2-dimensional Fourier transforming in accordance with the present invention. The results of the 2-dimensional Fourier transformation are supplied into a imaging section 6.

Instead of the 2-dimensional Fourier transformation, other mathematically equivalent techniques such as the fractional Fourier transformation or the Gabor transformation can be used to provide the same results.

The imaging section 6 calculates powers for the respective data (2-dimensional data) obtained from the 2-dimensional Fourier transformation, and produces an image using the powers as pixel values. This provides the direct vision image in the sound ray direction, i.e., the 3-dimensional image, representing the surface of the object to be imaged (e.g., a fetus).

Such a 3-dimensional image is superior in spatial resolution, because it is produced based on the 2-dimensional Fourier transformed data.

The quadrature detecting section 4, the 2-dimensional Fourier transforming section 5 and the imaging section 6 constitute means for producing images 10.

Also, the means for producing images 10 may be constructed to produce images based on the intensities of the received echo signals for the respective range gated sound rays without using the 2-dimensional Fourier transformation. Such means for producing images is desirable with regard to the simplification of the system.

The output image from the means for producing images 10 is supplied to a display section 7 and displayed as a visual image.

The range gating section 3, the quadrature detecting section 4, the 2-dimensional Fourier transforming section 5 and the imaging section 6 which are associated with the received echo signal processing have the operation speed sufficient to process the received echo signals in real-time for 4096 sound rays at the frame rate of 30 FPS, for example. Therefore, the image on the display section 7 is the real-time 3-dimensional image.

A control section 8 executes ultrasonic imaging according to the predetermined sequence by controlling the aforementioned components. The control section 8 is comprised of, for example, a computer.

An operating section 9 is connected to the control section 8. The operating section 9 is manipulated by an operator, and receives commands, imaging parameters and the like for the control section 8.

In above-described embodiments, the transducer array in the ultrasonic probe 1 is arranged in an 8×8 matrix. However, the matrix size is not limited thereto but any size may be selected, e.g., a 16×16 or 32×32 matrix.

As far as the operation speed at the range gating section 3, the quadrature detecting section 4, the 2-dimensional Fourier transforming section 5 and the imaging section 6 which are associated with the received echo signal processing permits, the matrix size is preferably selected as large as possible in order to obtain the wide imaging range or high resolution of the image.

When the large matrix size such as a 64×64 matrix is selected, it is preferred that a multiplexer is attached at the output of the transducer array, and the received echo signal processing, such as the beam forming and the like, is performed in time-sharing in order to avoid the large scale system. This technique is referred to as a "synthetic aperture" technique.

Figure 6:
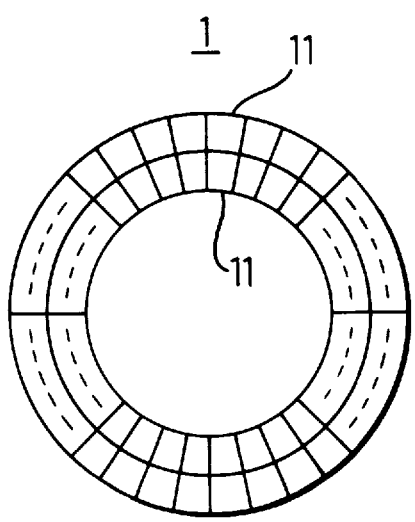
FIG. 6 is a view illustrating one example of a transducer array in an ultrasonic probe in an apparatus of one embodiment of the present invention.

Further, the arrangement of the transducer array is not necessarily limited to an exact rectangular matrix but simpler matrices can be used, an example of which is shown in FIG. 6. FIG. 6 illustrates one example of the array in which the ultrasonic transducer elements 11 are arranged in 2 concentric circles. Each row is comprised of, for example, 32 ultrasonic transducer elements.

Even if such a transducer array is used, a plurality of the receive beams which divides the small front view fr in the front view FR into, for example, an 8×8 matrix can be formed by the beam forming at the transmitting/receiving section 2.

Figure 7:
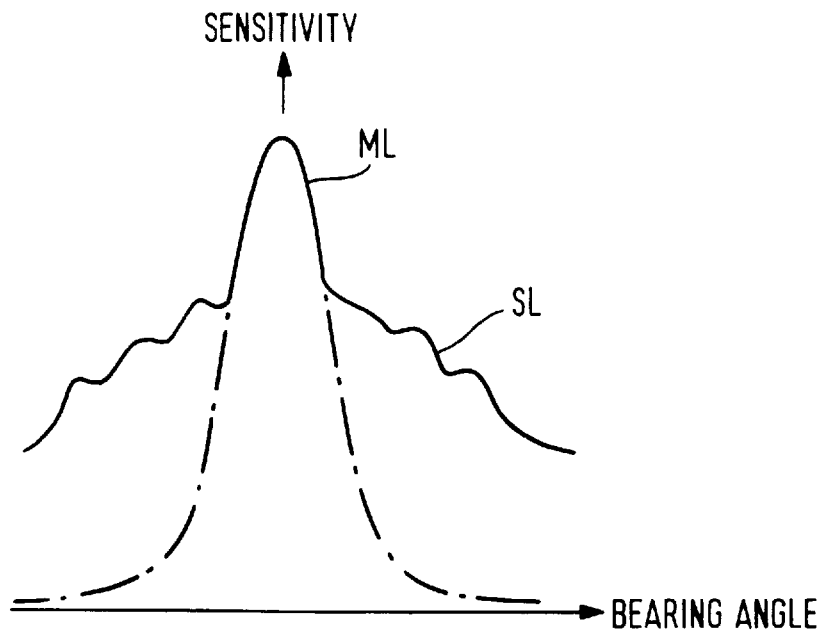
FIG. 7 illustrates the directionality of ultrasound beams.

However, the receive beam which is to be formed will have a large side lobes SL as shown in FIG. 7. But it is the acuteness of a main lobe ML that is important with respect to obtaining direct vision images in the sound ray direction, and the acuteness of the main lobe ML is almost the same as formed by the ideal beam forming (the dot-dashed lines), causing no problem.

Figure 8:
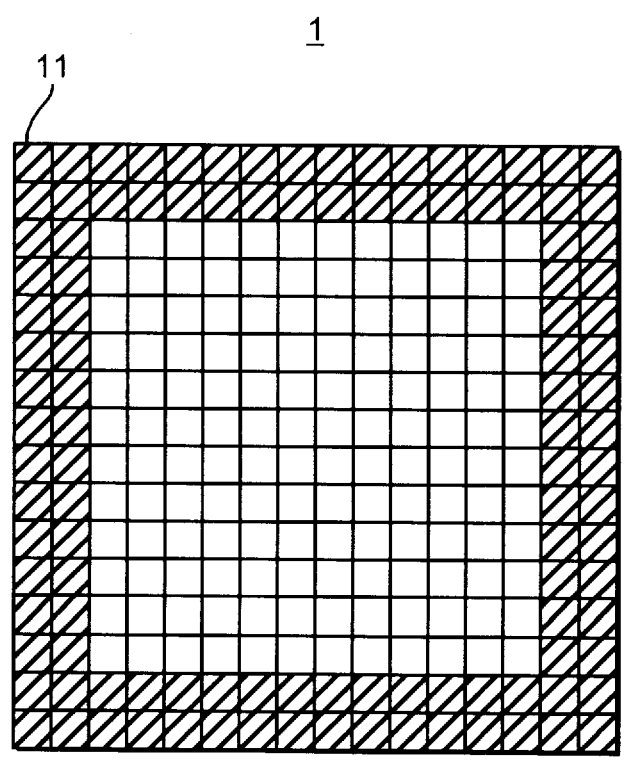
FIG. 8 is a view illustrating another example of a transducer array in an ultrasonic probe in an apparatus of one embodiment of the present invention.

Furthermore, the array may be shaped into a rectangular ring. The transducer elements on the peripherary of the rectangular matrix array may be used to arrange the rectangular ring-shaped array as shown in FIG. 8 as a hatched portion.

This technique is desirable, because the shape and size of the rectangular ring-shaped array can be unrestrictedly determined within the matrix according to the selection of the transducer elements.

Figure 9:
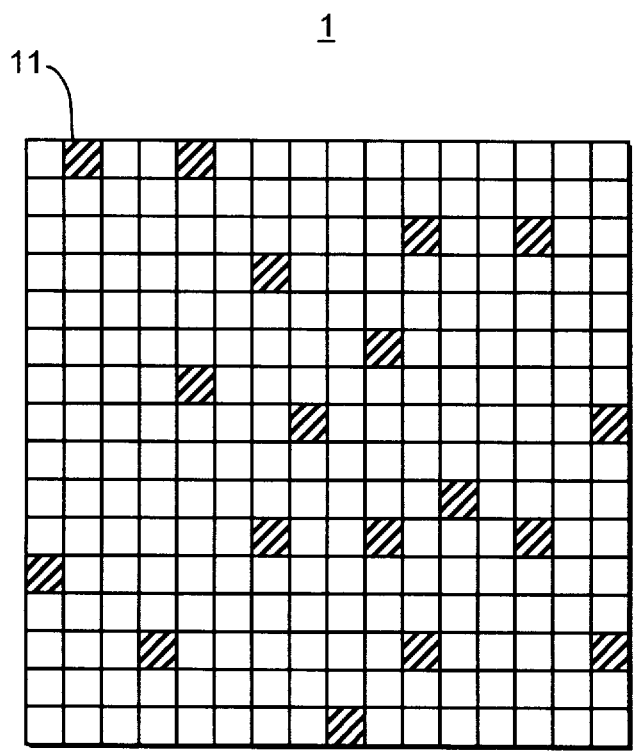
FIG. 9 is a view illustrating still another example of a transducer array in an ultrasonic probe in an apparatus of one embodiment of the present invention.

In addition, as shown in FIG. 9 as a hatched portion, the beam forming can be performed using the transducer arrangement in which the transducer elements associated with the beam forming are sparsely distributed in the matrix. Such an array is referred to as a "sparse array". The sparse array is desirable, because the degree of freedom of the array arrangement can be increased, benefited by the selection of the transducer elements.

When the rectangular ring-shaped array or sparse array is used, the receive beam to be formed by the beam forming will contain considerable side lobes, causing no problem for the reason described above.

Many widely different embodiments of the invention may be constructed without departing from the spirit and the scope of the present invention. It should be understood that the present invention is not limited to the specific embodiments described in the specification, except as defined in the appended claims.

What is claimed is:

1. An ultrasonic imaging method comprising the steps of:

defining a solid bearing angle subtending an object to be imaged;

dividing said solid bearing angle into a plurality of small solid bearing angles;

transmitting an ultrasonic wave into an interior of a subject having said object therein for each of said plurality of small solid bearing angles;

receiving concurrently a plurality of echoes from said object in each of said plurality of small solid bearing angles; and producing an image of said object at a predetermined depth thereof.

2. The method of claim 1, wherein said echoes are received ultrasonic waves and are range gated in a depth direction of said object.

3. The method of claim 2, wherein range gated signals are quadrature detected, and then, the quadrature detected signals are subjected to 2-dimensional Fourier transformation.

4. The method of claim 3, wherein said image of said object is obtained at a predetermined depth and thickness based on said range detected signals.

5. An apparatus for ultrasonic imaging, comprising:

means for defining a solid bearing angle subtending an object to be imaged;

means for dividing said solid bearing angle into a plurality of small solid bearing angles;

means for transmitting an ultrasonic wave into an interior of a subject having said object therein for each of said plurality of small solid bearing angles;

means for concurrently receiving a plurality of echoes from said object in each of said plurality of small solid bearing angles; and means for producing an image of said object at a predetermined depth thereof.

6. The apparatus of claim 5, wherein said means for concurrently receiving comprises means for receiving said echoes as ultrasonic waves, and means for range gating said received ultrasonic waves in a depth direction of said object.

7. The apparatus of claim 6, wherein said means for range gating comprises means for quadrature detecting said range gated signals, and means for subjecting the quadrature detected signals to 2-dimensional Fourier transformation.

8. The apparatus of claim 7, wherein said means for producing comprises means for obtaining said image of said object at a predetermined depth and thickness based on the range detected signals.

* * * * *